United States Patent
Trzecieski

(10) Patent No.: US 9,907,930 B2
(45) Date of Patent: Mar. 6, 2018

(54) AROMATHERAPY VAPORIZATION DEVICE

(71) Applicant: Michael Alexander Trzecieski, Toronto (CA)

(72) Inventor: Michael Alexander Trzecieski, Toronto (CA)

(*) Notice: Subject to any disclaimer, the term of this patent is extended or adjusted under 35 U.S.C. 154(b) by 0 days.

(21) Appl. No.: 15/287,038

(22) Filed: Oct. 6, 2016

(65) Prior Publication Data

US 2017/0095639 A1   Apr. 6, 2017

Related U.S. Application Data

(60) Provisional application No. 62/237,601, filed on Oct. 6, 2015.

(51) Int. Cl.
| | | |
|---|---|---|
| *A61M 15/00* | (2006.01) | |
| *A61M 21/00* | (2006.01) | |
| *A61M 21/02* | (2006.01) | |
| *A61L 9/03* | (2006.01) | |
| *A61M 11/04* | (2006.01) | |

(52) U.S. Cl.
CPC .......... *A61M 21/02* (2013.01); *A61M 11/042* (2014.02); *A61M 2021/0016* (2013.01); *A61M 2021/0066* (2013.01); *A61M 2205/3368* (2013.01); *A61M 2205/8206* (2013.01)

(58) Field of Classification Search
CPC .............. A61M 11/041; A61M 11/042; A61M 15/0001; A61M 15/0021; A61M 15/06; A61M 15/08; A61M 21/02; A61M 2021/0016; A61M 2021/0066; A61M 2205/3368; A61M 2205/8206; A61L 9/03; A24F 47/008

See application file for complete search history.

(56) References Cited

U.S. PATENT DOCUMENTS

| | | | | |
|---|---|---|---|---|
| 5,564,442 A | * | 10/1996 | MacDonald | A24F 47/008 131/194 |
| 7,186,958 B1 | * | 3/2007 | Nelson | A61M 11/041 128/200.23 |
| 8,739,786 B2 | * | 6/2014 | Postma | A61M 11/041 128/203.23 |
| 2008/0121244 A1 | * | 5/2008 | Bryman | A24F 47/004 131/328 |

(Continued)

*Primary Examiner* — Darren W Gorman
(74) *Attorney, Agent, or Firm* — Bereskin & Parr LLP/S.E.N.C.R.L., s.r.l.

(57) ABSTRACT

A novel aromatherapy vaporization device is disclosed having a heating chamber first portion for receiving of phyto material and a heating chamber second portion. In a first mode of operation phyto material is loaded into the heating chamber first portion having a first conductive heating element disposed therein and in a second mode of operation an angle of a hinge is varied that brings the heating chamber second portion in proximity to the heating chamber first portion. In the second mode of operation electrical current flows from a first battery to a first conductive heating element and the phyto material is heated to a predetermined temperature and vapor is emitted from the heating of the phyto material and is captured in the heating chamber second portion and flows through a heating chamber first portion aperture and propagates through a fluid pathway for inhalation from an inhalation aperture.

21 Claims, 3 Drawing Sheets

(56) References Cited

U.S. PATENT DOCUMENTS

| | | | |
|---|---|---|---|
| 2008/0216824 A1* | 9/2008 | Ooida | A61M 15/02 |
| | | | 128/200.21 |
| 2011/0120482 A1* | 5/2011 | Brenneise | A24F 47/008 |
| | | | 131/328 |
| 2012/0325227 A1* | 12/2012 | Robinson | A61M 15/06 |
| | | | 131/328 |
| 2013/0174842 A1* | 7/2013 | Young | A61L 9/032 |
| | | | 128/203.14 |
| 2014/0041655 A1* | 2/2014 | Barron | A61M 11/042 |
| | | | 128/202.21 |
| 2014/0373857 A1* | 12/2014 | Steinberg | A24F 47/008 |
| | | | 131/329 |

* cited by examiner

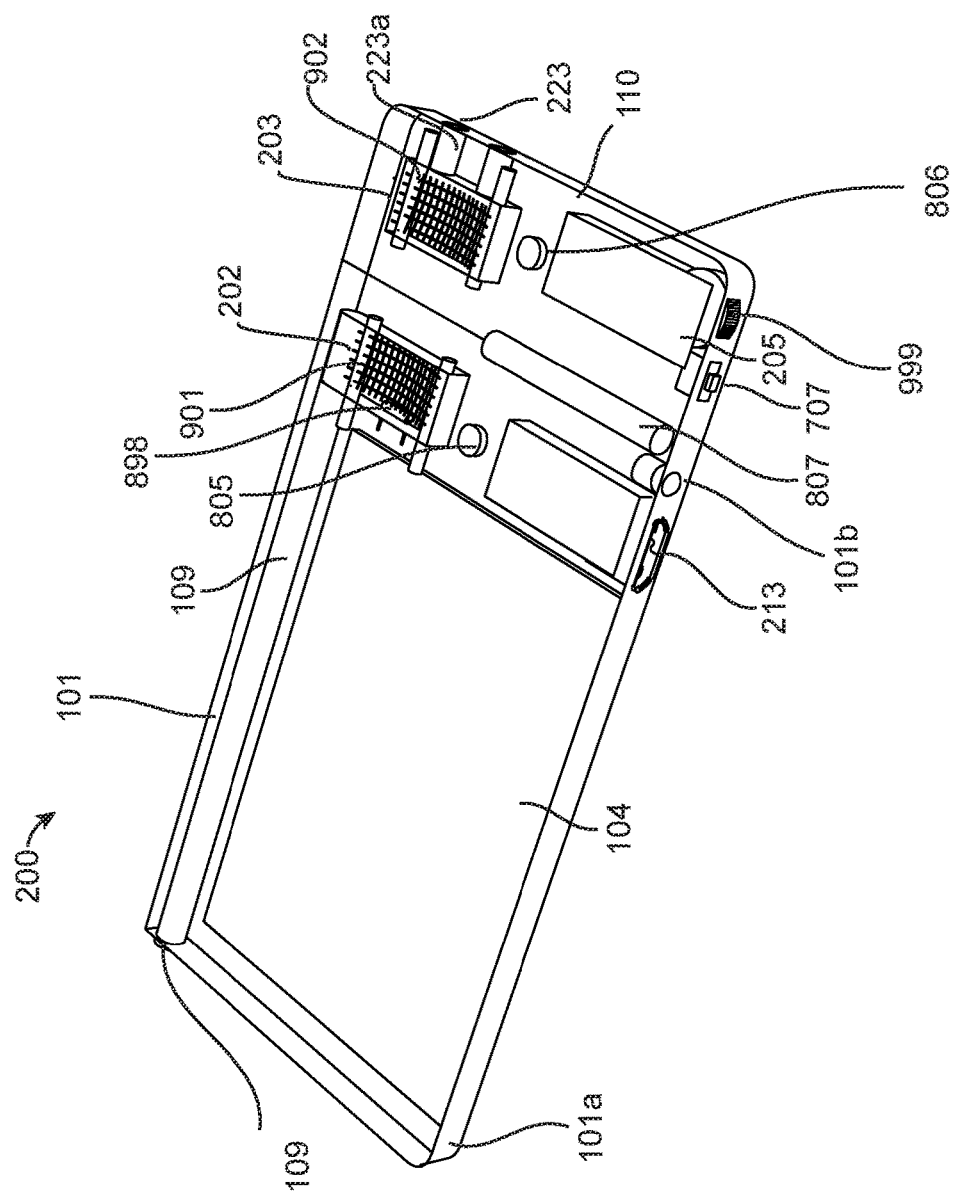

AROMATHERAPY VAPORIZATION DEVICE

CROSS REFERENCE TO RELATED APPLICATION

This application benefits from the priority of U.S. Provisional Applications 62/237,601 filed on Oct. 6, 2015, which is incorporated herein by reference.

TECHNICAL FIELD OF THE INVENTION

The technical field relates to a device for vaporization of phyto materials and more specifically to a device for aromatherapy vaporization.

BACKGROUND OF THE INVENTION

Aromatherapy generally uses essential oils, which are extracted from phyto materials, such as leaves of plants, for therapeutic benefits. These essential oils are either massaged into the skin or can be inhaled. In some cases the phyto materials are heated in order to released the essential oils therefrom. By heating these phyto materials at predetermined temperatures, essential oils and extracts are boiled off, depending upon the temperature at which these phyto materials are heated, an aroma or vapor is given off, which is then inhaled by a user for its therapeutic benefits. Devices that provide such operation are generally known as vaporizers. Different phyto materials release vapors at different temperatures. Some release vapors at 120 degrees Celsius, whereas others at 220 degrees Celsius. Ideally the predetermined temperature is less than a combustion temperature of the phyto material or loose leaf material.

Many herbal vaporization devices on the market utilize a heating chamber in order to heat herbal leaf material in order to vaporize its contents so that desired oils and other flavor materials can be separated from the leaf material in order to be consumed by a user of the device in a vaporized form.

Unfortunately, many of these herbal vaporization devices have long heating times as well as are large in size and are not convenient to be carried around.

It is therefore an object of the invention to provide an aromatherapy vaporization device that overcomes the aforementioned deficiencies.

SUMMARY

In accordance with the embodiments of the invention there is provided an aromatherapy vaporization adapted to fit into a pocket comprising: a housing first portion having a housing first portion first surface, the housing first portion coupled with a hinge to a housing second portion having a housing second portion first surface, the housing second portion for operating in a first mode of operation where the housing first portion first surface and the housing second portion first surface are inline and an angle of the hinge is at an approximately 180 degrees as measured between the housing first portion first surface and the housing second portion first surface and for operating in a second mode of operation where the angle of the hinge is at an approximately 2 degrees and the housing first portion first surface and the housing second portion first surface are facing opposite each other, the housing first portion having an inhalation aperture disposed proximate a first end thereof and comprising a second end opposite the first end; a heating chamber first portion disposed proximate the second end of the housing first portion having a first conductive heating element disposed therein; a fluid pathway disposed between the inhalation aperture and the heating chamber first portion; a heating chamber second portion disposed in the housing second portion, for in the second mode of operation the heating chamber second portion and the heating chamber first portion form an approximately closed heating chamber having an ambient air input port; a heating chamber first portion aperture for fluidly coupling of the heating chamber first portion with the fluid pathway; a first battery disposed within the housing first portion; a first control circuit electrically coupled with the first battery; a first conductive heating element disposed within the heating chamber first portion electrically coupled with the first control circuit; a switch electrically coupled with the first control circuit for generating a switch control signal, the heating chamber first portion for receiving of phyto material in the first mode of operation and for heating of the phyto material in the second mode of operation, wherein, in a transition from the first mode of operation to the second more of operation an angle of the hinge is decreased and in use, in the second mode of operation upon depressing of the switch, electrical current flows from the first battery to the first conductive heating element and the phyto material is heated to a predetermined temperature and vapor is emitted from the heating of the phyto material and is captured in the heating chamber second portion and flows through the heating chamber first portion aperture and propagates through the fluid pathway for inhalation from the inhalation aperture.

In accordance with the embodiments of the invention there is provided an aromatherapy vaporization device adapted to fit into a pocket comprising a housing first portion having a housing first portion first surface, the housing first portion coupled with a hinge to a housing second portion having a housing second portion first surface, the housing second portion for operating in a first mode of operation where the housing first portion first surface and the housing second portion first surface are approximately inline and an angle of the hinge as measured between the housing first portion first surface and the housing second portion first surface is at an approximately 180 degrees and for operating in a second mode of operation where the angle of the hinge is at an approximately 2 degree angle and the housing first portion first surface and the housing second portion first surface are facing opposite each other, the housing first portion having an inhalation aperture disposed proximate a first end thereof and comprising a second end opposite the first end; a heating chamber first portion disposed proximate the second end of the housing first portion having a first conductive heating element disposed therein; a fluid pathway disposed between the inhalation aperture and the heating chamber first portion; a heating chamber second portion disposed in the housing second portion, for in the second mode of operation the heating chamber second portion and the heating chamber first portion form an approximately closed heating chamber having an ambient air input port; a heating chamber first portion aperture for fluidly coupling of the heating chamber first portion with the fluid pathway; a first battery disposed within the housing first portion; a first control circuit electrically coupled with the first battery; a first conductive heating element disposed within the heating chamber first portion electrically coupled with the first control circuit; a first electrical contact disposed within the first housing portion and protruding through the housing first portion first surface and electrically coupled with the first control circuit; a second electrical contact disposed within the second housing portion and protruding through the housing second portion first surface and electrically coupled with the first control circuit, the heating chamber first portion for receiving of phyto material in the first mode of operation and for heating of the phyto material in the second mode of operation, wherein, in use, an angle of the hinge is varied and in the second mode of operation the first electrical contact and the second electrical contact are electrically coupled with each other and electrical current flows from the first battery to the first conductive heating element and the phyto material is heated to a predetermined temperature and vapor is emitted from the heating of the phyto material and is captured in the heating chamber second portion and flows through the heating chamber first portion aperture and propagates through the fluid pathway for inhalation from the inhalation aperture.

BRIEF DESCRIPTION OF THE DRAWINGS

FIG. 1E illustrates the AVD in accordance with a second embodiment of the invention.

DETAILED DESCRIPTION OF EMBODIMENTS

For the purposes of this detailed description, the term loose leaf herbal material is categorized as phyto material 419 and includes phyto material extract, where the phyto material extract is derived from the phyto material 419 or from the loose leaf herbal material.

Figure 1A:
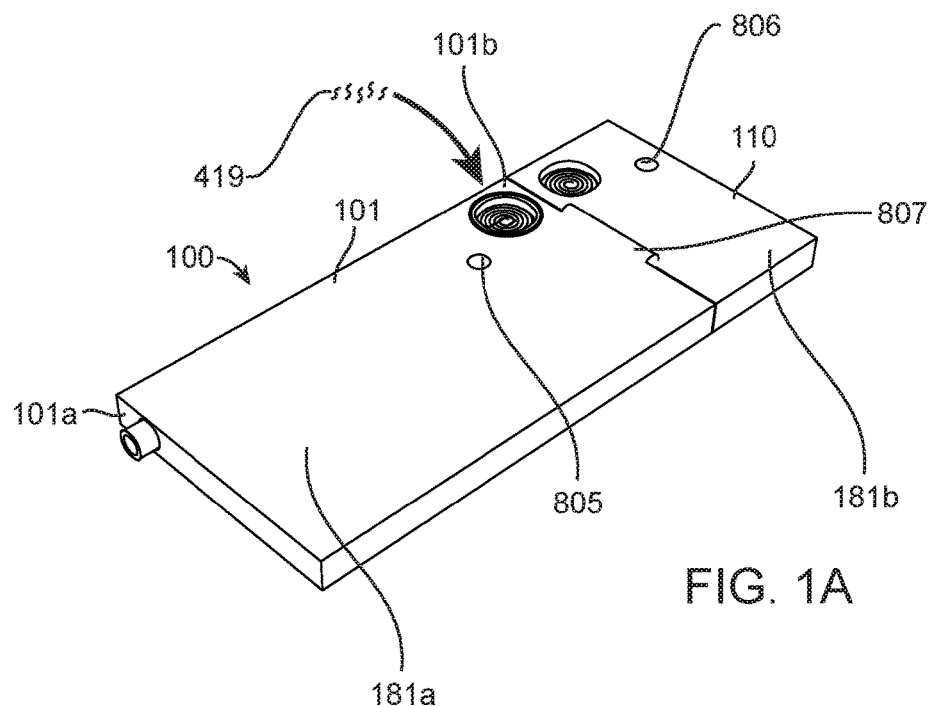
FIG. 1A illustrates an aromatherapy vaporization device (AVD) in accordance with a first embodiment of the invention.

FIG. 1A illustrates an aromatherapy vaporization device (AVD) 100 in accordance with a first embodiment of the invention and in a first mode of operation. The AVD 100 is formed from a housing first portion 101 having a housing first portion first surface 181*a*, the housing first portion 101 coupled with a hinge 807 to a housing second portion 110 having a housing second portion first surface 181*b*. In the first mode of operation the housing first portion first surface 181*a* and the housing second portion first surface 181*b* are approximately inline. An angle of the hinge as measured between the housing first portion first surface 181*a* and the housing second portion first surface 181*b* is at an approximately 180 degrees (FIG. 1A) and for operating in a second mode of operation (FIG. 1D) where the angle of the hinge is at an approximately 2 degree and the housing first portion first surface 181*a* and the housing second portion first surface 181*b* are facing opposite each other.

Figure 1B:
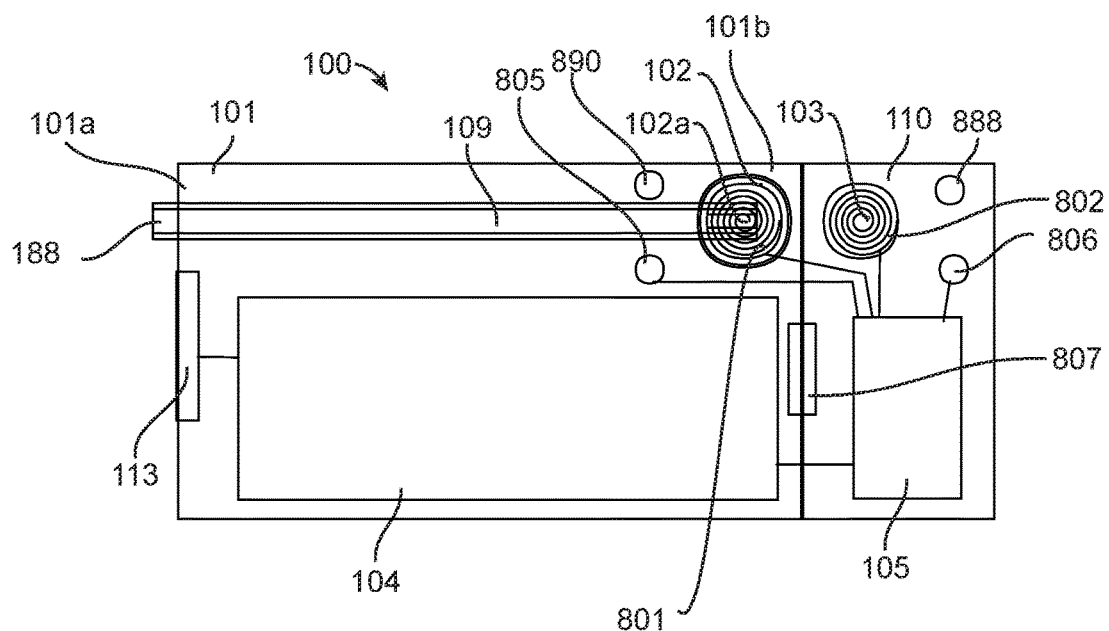
FIG. 1B illustrates the AVD in a first mode of operation from a top view where the housing first portion first surface and the housing second portion first surface are removed for clarity

Referring to FIG. 1B, the AVD 100 is shown in the first mode of operation from a top view where the housing first portion first surface 181*a* and the housing second portion first surface 181*b* are removed for clarity. As is illustrated, the housing first portion 101 has an inhalation aperture 188 disposed proximate a first end 101*a* thereof and has a second end 101*b* opposite the first end 101*a*. A heating chamber first portion 102 is disposed proximate the second end 101*b* of the housing first portion 101 having a first conductive heating element 801 disposed therein. A fluid pathway 109 is disposed between the inhalation aperture 188 and the heating chamber first portion 102.

A heating chamber first portion aperture 102*a* is provided for fluidly coupling of the heating chamber first portion 102 with the fluid pathway 109. A first battery 104 disposed within the housing first portion, wherein preferably the battery is a lithium polymer battery. A first control circuit 105 electrically coupled with the first battery 104 and a first conductive heating element 801, which is disposed within the heating chamber first portion 101. A first electrical contact 805 is disposed within the first housing portion 101 and protruding through the housing first portion first surface 181*a* and electrically coupled with the first control circuit 105. A second electrical contact 806 is disposed within the second housing portion 110 and protruding through the housing second portion first surface 181*b* and is also electrically coupled with the first control circuit 105.

The heating chamber first portion 102 is for receiving of phyto material 419 in the first mode of operation and for heating of the phyto material 419 in the second mode of operation. A transition from the first mode of operation into the second mode of operation of the AVD 100 is shown in FIG. 1C where the angle of the hinge is reduced in the transition.

Figure 1C:
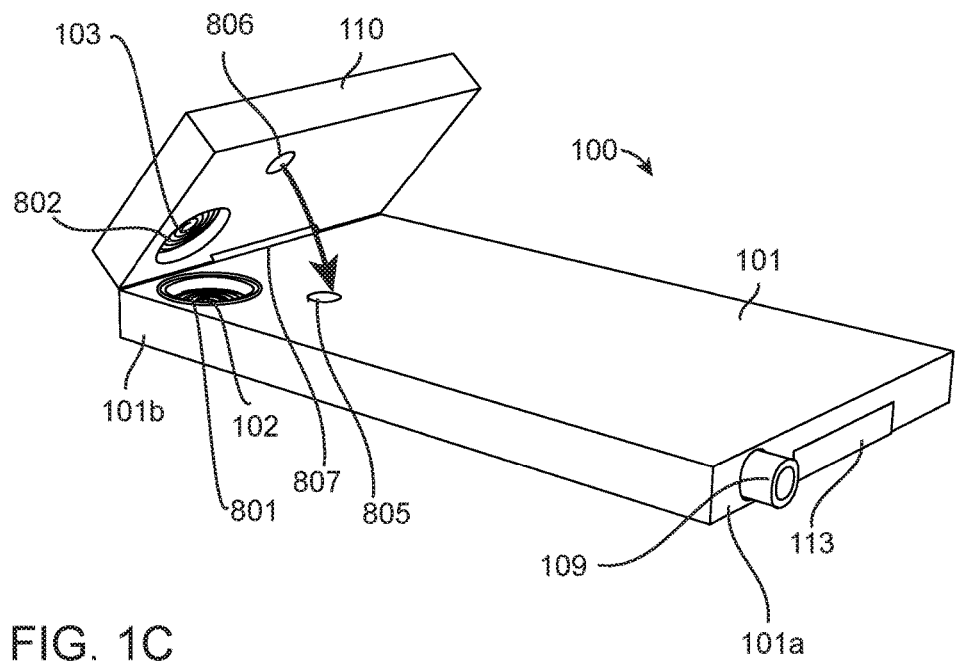
FIG. 1C illustrates a transition from the first mode of operation into the second mode of operation of the AVD.
Figure 1D:
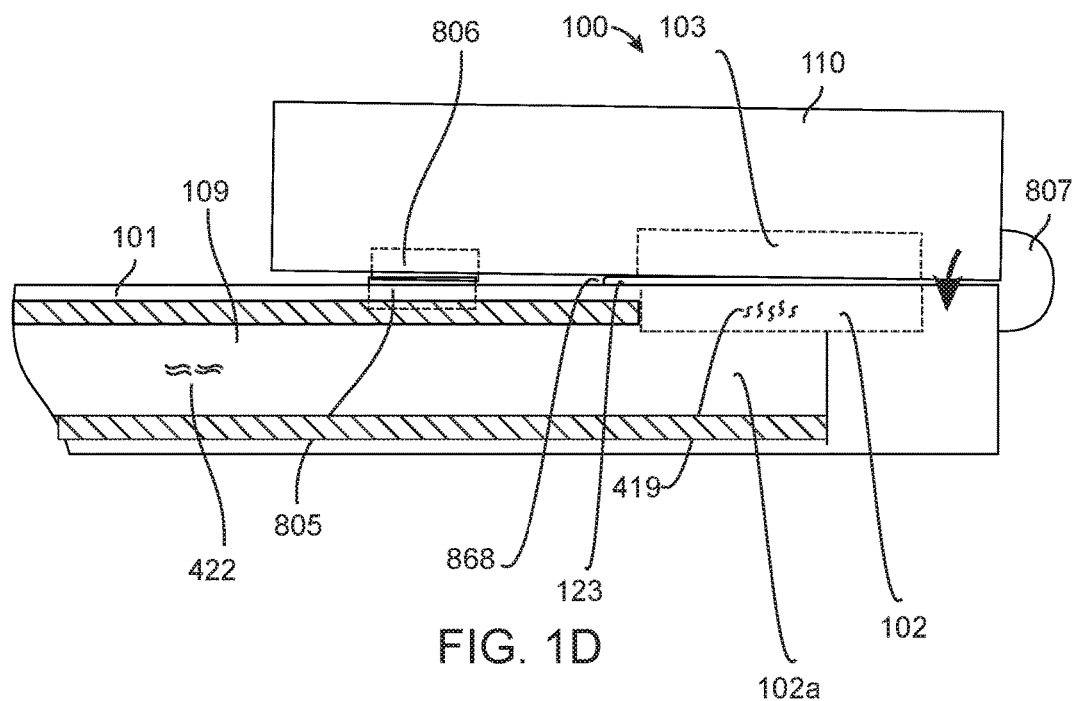
FIG. 1D illustrates the AVD with a heating chamber second portion and a heating chamber first portion forming an approximately closed heating chamber.

A heating chamber second portion 103 is disposed in the housing second portion 110, for in the second mode of operation, as is shown in FIG. 1D, the heating chamber second portion 103 and the heating chamber first portion 102 form an approximately closed heating chamber having an ambient air input port 123. As is illustrated in FIG. 1D, a gap 868 is formed between the heating chamber first portion 102 and the heating chamber second portion 103 for allowing of ambient air to enter into the heating chamber first and second portions 102 and 103.

In use, in the second mode of operation, the first electrical contact 805 and the second electrical contact 806 are electrically coupled with each other and electrical current flows from the first battery 104 to the first conductive heating element 801 and the phyto material 419 is heated to a predetermined temperature, such as 160 degrees Celsius to 230 degrees Celsius, and vapor 422 is emitted from the heating of the phyto material 419 and is captured in the heating chamber second portion 103 and flows through the heating chamber first portion aperture 102*a* and propagates through the fluid pathway 109 for inhalation from the inhalation aperture 188. In the second mode of operation the hinge is at an approximately 2 degree angle and the housing first portion first surface 181*a* and the housing second portion first surface 181*b* are facing opposite each other with the phyto material 419 disposed therebetween.

Referring to FIGS. 1B and 1C, a second conductive heating element 802 is disposed within the heating chamber second portion 103 and electrically coupled with the control circuit 105, wherein in the second mode of operation at least one of the first conductive heating element 801 and the second conductive heating element 802 heat the phyto material 419 for the releasing of vapor 422 therefrom. Furthermore as shown in FIG. 1B, disposed proximate to the at least one of the first electrical contact 805 and the second electrical contact 806 is at least a first magnet 888 and a second magnet 890. The at least a first magnet 888 and a second magnet 890 operate in order to maintain the AVD 100 in the second mode of operation. In the case where there is one of the a first magnet 888 and a second magnet 890, a metal plate is used and disposed on the opposite side for providing for a magnetic coupling to result.

Preferably the fluid pathway 109 comprises a thermally conductive material to cool the vapor and air propagating therethrough to a temperature that is comfortable for inhalation by a user. So for example the thermally conductive material comprises aluminum or copper or stainless steel and a temperature that is comfortable for inhalation for the user is approximately under fifty degrees Celsius.

Preferably at least one of the first and second conductive heating elements 801 and 802 are manufactured from a low thermal inertia conductive heating element and comprises a metal material that comprises a nickel metal alloy. Optionally a ceramic pancake heater is also envisaged for at least one of the first and second conductive heating elements 801 and 802. Having a low thermal inertia conductive heating element allows for quick heating and is advantageous when the user is impatient.

Because the first embodiment of the invention uses conduction heating to heat the phyto material 419, preferably the phyto material 419 is compressed between the heating chamber first portion and the heating chamber second portion 102 and 103 in the second mode of operation.

Referring to FIG. 1B, preferably the housing first portion comprises a recharging port 113 electrically coupled with the first battery 104 for receiving of electrical current for recharging thereof. Having the ability to recharge the first battery 104 is not essential, however if this recharging port 113 is not provided then the AVD 100 becomes a disposable device. The AVD 100 as such therefore starts to heat the phyto material 419 upon the housing first portion first surface 181a and the housing second portion first surface 181b facing each other with the first and second electrical contacts 805 and 806 are in electrical communication with each other and stops heating when the first and second electrical contacts 805 and 806 are other than in electrical communication with each other. This allows the user to customize their experience by opening and closing of the housing first portion 101 with respect to the housing second portion 110. The holding together of the housing first portion 101 with respect to the housing second portion 110 can be performed either manually by the user in the second mode of operation or the magnets are utilized to maintain an attraction between the housing first portion 101 and the housing second portion 110.

FIG. 1E illustrates an AVD 200 in accordance with a second embodiment of the invention and in a first mode of operation. Shown in FIG. 1E, is a temperature sensor 898 that is thermally coupled proximate one of a heating chamber first portion 202 and a heating chamber second portion 203. The AVD 100 is formed from the housing first portion 101 having a housing first portion first surface 181a, which is removed for clarity in this drawing, the housing first portion 101 coupled with a hinge 807 to a housing second portion 110 having a housing second portion first surface 181b, which is removed in this figure for clarity. In the first mode of operation the hinge 807 is at an approximately 180 degrees angle. The housing first portion 101 includes a recharging port 213 electrically coupled with the first battery 104, in this embodiment the recharging port 113 is a micro USB port, however a USB C port is also envisaged. A first control circuit 205 is provided and electrically coupled with the first battery 104 and also coupled with at least one of a first conductive heating element 901 and a second conductive heating element 902. In this embodiment, a temperature adjustment dial 999 is provide and electrically coupled with the first control circuit 205 for in combination with the temperature sensor 898 for providing a controlled heating to the at least one of the first conductive heating element 901 and the second conductive heating element 902. Providing of controlled heating allows for heating of the phyto material 419 in such a manner that combustion thereof is potentially avoided. The temperature adjustment dial 999 is for example formed from a variable resistor that provides a variable resistance to the first control circuit 205 for analog temperature adjustment of the first and second conductive heating elements 901 and 902.

A switch 707 is also optionally provided and electrically coupled with the first control circuit 205 for enabling and disabling the provision of controlled heating to the at least one of the first conductive heating element 901 and the second conductive heating element 902 in dependence upon a switch control signal.

An ambient air input port 223 is provided and in fluid communication with the second conductive heating element 902, where optionally there is a one-way airflow valve 223a, such as an umbrella valve, to allow air to flow only in a single direction into the heating chamber first and second portions 202 and 203 when in the second mode of operation. Preferably with the use of the one-way airflow valve 223a, there is a high temperature silicone rubber seal disposed between the heating chamber first and second portions 202 and 203 so that the vapor and ambient air 422 does not flow out of the heating chamber first and second portions 202 and 203 when in the second mode of operation other than flowing through the fluid pathway 109.

Preferably at least one of the first and second conductive heating elements 901 and 902 are manufactured from a low thermal inertia conductive heating element that comprises a metal mesh as is shown in FIG. 1E.

Preferably the battery is lithium polymer battery. There are some lithium polymer batteries that are approximately 1 mm thick. The conductive heating element in accordance with the embodiments of the invention is made from a thin nickel containing resistive metal plate or a thin nickel containing resistive mesh as is shown in FIG. 1E for the first and second conductive heating elements 901 and 902 where preferably the thickness is about 0.1 mm. A spiral or coil heating element is also envisaged or also a ceramic pancake heater element as options.

In the first mode of operation because the heating chamber first and second portions 102 and 103 are other than coupled together, it makes for easy cleaning and emptying of vaporized phyto material that is leftover within the heating chamber first and second portions 102 and 103.

It is advantageous to have a vaporizer that is a small form factor as well as one that is discrete to bring along for various adventures. It is envisaged that the vaporization device in accordance with the embodiments of the invention is about 5 mm thick and has a size of about 80 mm×50 mm. Of course, if possible a thickness of less than 3 mm is also envisaged where it can be stored in a wallet because the size resembles that of a pair of credit cards stacked together. Also one that provides for easy cleaning and for having the vapor that is emitted therefrom to not be too hot for inhalation by the end user.

Numerous other embodiments are envisaged without departing from the spirit or scope of the invention

What I claim is:

1. An aromatherapy vaporization device adapted to fit into a pocket comprising:
a housing first portion having a housing first portion first surface, the housing first portion coupled with a hinge to a housing second portion having a housing second portion first surface, the housing second portion for operating in a first mode of operation where the housing first portion first surface and the housing second portion first surface are approximately inline and an angle of the hinge as measured between the housing first portion first surface and the housing second portion first surface is at an approximately 180 degrees and for operating in a second mode of operation where the angle of the hinge is at an approximately 2 degree angle and the housing first portion first surface and the housing second portion first surface are facing opposite each other, the housing first portion having an inhalation aperture disposed proximate a first end thereof and comprising a second end opposite the first end;

a heating chamber first portion disposed proximate the second end of the housing first portion having a first conductive heating element disposed therein;

a fluid pathway disposed between the inhalation aperture and the heating chamber first portion;

a heating chamber second portion disposed in the housing second portion, wherein in the second mode of operation the heating chamber second portion and the heating chamber first portion form an approximately closed heating chamber having an ambient air input port;

a heating chamber first portion aperture for fluidly coupling the heating chamber first portion with the fluid pathway;

a first battery disposed within the housing first portion;

a control circuit electrically coupled with the first battery;

the first conductive heating element disposed within the heating chamber first portion electrically coupled with the control circuit;

a first electrical contact disposed within the housing first portion and protruding through the housing first portion first surface and electrically coupled with the control circuit;

a second electrical contact disposed within the housing second portion and protruding through the housing second portion first surface and electrically coupled with the control circuit, the heating chamber first portion for receiving phyto material in the first mode of operation and for heating the phyto material in the second mode of operation, wherein, in use, an angle of the hinge is varied and in the second mode of operation the first electrical contact and the second electrical contact are electrically coupled with each other and electrical current flows from the first battery to the first conductive heating element and the phyto material is heated to a predetermined temperature and vapor is emitted from the heating of the phyto material and is captured in the heating chamber second portion and flows through the heating chamber first portion aperture and propagates through the fluid pathway for inhalation from the inhalation aperture.

2. An aromatherapy vaporization device according to claim 1 comprising a second conductive heating element disposed within the heating chamber second portion and electrically coupled with the control circuit, wherein in the second mode of operation at least one of the first conductive heating element and the second conductive heating element are used for heating the phyto material.

3. An aromatherapy vaporization device according to claim 1 wherein the fluid pathway comprises a thermally conductive material to cool the vapor and air propagating through the fluid pathway to a temperature that is comfortable for inhalation by a user and under fifty degrees Celsius.

4. An aromatherapy vaporization device according to claim 2 wherein at least one of the first conductive heating element and the second conductive heating element comprises a low thermal inertia conductive heating element.

5. An aromatherapy vaporization device according to claim 1 wherein the first conductive heating element comprises a low thermal inertia conductive heating element.

6. An aromatherapy vaporization device according to claim 1 wherein the housing first portion comprises a recharging port electrically coupled with the first battery for receiving electrical current for recharging the first battery.

7. An aromatherapy vaporization device according to claim 1 comprising a temperature sensor thermally coupled proximate one of the heating chamber first portion and the heating chamber second portion.

8. An aromatherapy vaporization device according to claim 1 wherein the ambient air input port comprises a gap between the heating chamber first portion and the heating chamber second portion when in the second mode of operation and allows for ambient air to flow through the gap.

9. An aromatherapy vaporization device according to claim 1 wherein the first conductive heating element comprises a ceramic pancake heater.

10. An aromatherapy vaporization device according to claim 1 comprising: at least a first magnet and a second magnet disposed proximate the first electrical contact and the second electrical contact, respectively, for maintaining the aromatherapy vaporization device in the second mode of operation.

11. An aromatherapy vaporization device according to claim 7 comprising:
a second conductive heating element disposed within the heating chamber second portion and electrically coupled with the control circuit; and
a temperature adjustment dial electrically coupled with the control circuit and the temperature sensor for providing a controlled heating to at least one of the first conductive heating element and the second conductive heating element.

12. An aromatherapy vaporization device according to claim 2 comprising: a switch electrically coupled with the control circuit for enabling and disabling the provision of controlled heating to the at least one of the first conductive heating element and the second conductive heating element.

13. An aromatherapy vaporization device according to claim 4 wherein the low thermal inertia conductive heating element comprises a metal mesh.

14. An aromatherapy vaporization adapted to fit into a pocket comprising:
a housing first portion having a housing first portion first surface, the housing first portion coupled with a hinge to a housing second portion having a housing second portion first surface, the housing second portion for operating in a first mode of operation where the housing first portion first surface and the housing second portion first surface are inline and an angle of the hinge is at approximately 180 degrees as measured between the housing first portion first surface and the housing second portion first surface and for operating in a second mode of operation where the angle of the hinge is at approximately 2 degrees and the housing first portion first surface and the housing second portion first surface are facing opposite each other,
the housing first portion having an inhalation aperture disposed proximate a first end thereof and comprising a second end opposite the first end;

a heating chamber first portion disposed proximate the second end of the housing first portion having a first conductive heating element disposed therein;

a fluid pathway disposed between the inhalation aperture and the heating chamber first portion;

a heating chamber second portion disposed in the housing second portion, wherein in the second mode of operation the heating chamber second portion and the heating chamber first portion form an approximately closed heating chamber having an ambient air input port;

a heating chamber first portion aperture for fluidly coupling the heating chamber first portion with the fluid pathway;

a first battery disposed within the housing first portion;

a control circuit electrically coupled with the first battery;

the first conductive heating element disposed within the heating chamber first portion electrically coupled with the control circuit;

a switch electrically coupled with the control circuit for generating a switch control signal;

the heating chamber first portion for receiving phyto material in the first mode of operation and for heating the phyto material in the second mode of operation, wherein, in a transition from the first mode of operation to the second mode of operation an angle of the hinge is decreased and in use, in the second mode of operation upon depressing of the switch, electrical current flows from the first battery to the first conductive heating element and the phyto material is heated to a predetermined temperature and vapor is emitted from the heating of the phyto material and is captured in the heating chamber second portion and flows through the heating chamber first portion aperture and propagates through the fluid pathway for inhalation from the inhalation aperture.

15. An aromatherapy vaporization device according to claim 14 comprising a one-way airflow valve to allow ambient air to flow only in a single direction into the heating chamber first and second portions through the ambient air input port.

16. An aromatherapy vaporization device according to claim 15 comprising a high temperature silicone rubber seal disposed between the heating chamber first and second portions whereby the vapor and ambient air do not flow out of the heating chamber first and second portions.

17. An aromatherapy vaporization device according to claim 14 comprising: a second conductive heating element disposed within the heating chamber second portion and electrically coupled with the control circuit, wherein in the second mode of operation at least one of the first conductive heating element and the second conductive heating element are used for heating the phyto material.

18. An aromatherapy vaporization device according to claim 14 comprising a temperature sensor thermally coupled proximate one of the heating chamber first portion and the heating chamber second portion.

19. An aromatherapy vaporization device according to claim 18 comprising:

a second conductive heating element disposed within the heating chamber second portion and electrically coupled with the control circuit; and a temperature adjustment dial electrically coupled with the control circuit and the temperature sensor for providing a controlled heating to at least one of the first conductive heating element and the second conductive heating element.

20. An aromatherapy vaporization device according to claim 4 wherein the low thermal inertia conductive heating element comprises a nickel metal alloy.

21. An aromatherapy vaporization device according to claim 5 wherein the low thermal inertia conductive heating element comprises a nickel metal alloy.

* * * * *